United States Patent [19]

Jones et al.

[11] 4,166,819
[45] Sep. 4, 1979

[54] 4-AROYL SUBSTITUTED PHENOXY METHYLENE-5-TETRAZOLES

[75] Inventors: Peter H. Jones, Lake Forest, Ill.; Dilbagh S. Bariana, Montreal; Anthony K. L. Fung, Pierrefonds, both of Canada; Yvonne C. Martin, Waukegan, Ill.; Jaroslav Kyncl, Lake Bluff, Ill.; Amrit Lall, Libertyville, Ill.

[73] Assignee: Abbott Laboratories, North Chicago, Ill.

[21] Appl. No.: 830,975

[22] Filed: Sep. 6, 1977

Related U.S. Application Data

[62] Division of Ser. No. 616,220, Sep. 24, 1975, Pat. No. 4,058,559.

[51] Int. Cl.$^2$ ............................................ C07D 257/04
[52] U.S. Cl. ..................................................... 548/253
[58] Field of Search .................................... 260/308 D

[56] References Cited

U.S. PATENT DOCUMENTS 3,515,727  6/1970  Garbecht ..................... 260/308 D

FOREIGN PATENT DOCUMENTS 2508852  9/1975  Fed. Rep. of Germany ...... 260/308 D

Primary Examiner—Donald G. Daus
Assistant Examiner—D. B. Springer
Attorney, Agent, or Firm—Robert L. Niblack; Gildo E. Fato

[57] ABSTRACT

This invention provides 4-aroyl substituted phenoxy acetic acids and tetrazoles of the formula

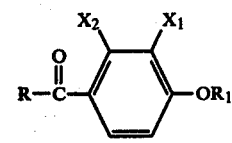

wherein R is a phenyl ring, a substituted phenyl ring, or naphthyl; $R_1$ is —$CH_2COOH$ or methyl tetrazole, and $X_1$ and $X_2$ are each a halogen or loweralkyl, or when taken together form with the two attached carbons a phenyl ring.

These compounds are useful as antihypertensive agents, diuretics and uricosuric agents.

3 Claims, No Drawings

4-AROYL SUBSTITUTED PHENOXY METHYLENE-5-TETRAZOLES

This is a division, of application Ser. No. 616,220 filed Sept. 24, 1975 now U.S. Pat. No. 4,058,559.

DESCRIPTION OF THE INVENTION

The present invention is related to the treatment of (1) all types of hypertension, (2) edema of all types (e.g., congestive heart failure, pulmonary edema, nephrosis, ascites, pre-menstrual tension, pregnancy, etc.), diminished kidney function, (3) hyperuricemia due to any cause, (4) an adjuvant to therapy with drugs which are lost due to rapid renal excretion, and (5) in the treatment of diabetes insipidus.

It may also be used to promote the excretion of excess fluids, electrolytes, toxic drugs and chemicals. This combination of effects represents a valuable new tool in the treatment of hypertension, edema, hyperuricemia, diabetes insipidus, fluid and electrolyte accumulation and poisoning with various toxic agents.

It is thus an object of this invention to provide a composition for treatment of hypertension in warm-blooded animals; to provide a composition for the treatment of hyperuricemia; to provide a composition for treatment of various forms of edema including congestive heart failure. In conjunction with these objects, it is an object of this invention to provide a diuretic composition in dosage unit form that virtually avoids all dangers of over-dosing with toxic side effects and diabetes insipidus.

These and other objects are accomplished by providing a medicinal composition consisting essentially of a 4-aroyl substituted phenoxy acetic acid or tetrazole represented by formula (I):

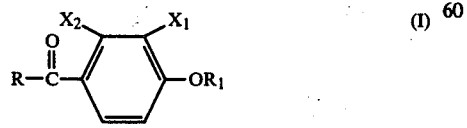

(I)

wherein R is a phenyl ring, a substituted phenyl ring, or naphthyl; $R_1$ is —$CH_2COOH$ or methyl tetrazole; and $X_1$ and $X_2$ are each a halogen or loweralkyl, or when taken together form with the two attached carbons a phenyl ring.

As used herein, the term "halogen" means chlorine, bromine, fluorine or iodine.

The term "loweralkyl" means saturated, monovalent, aliphatic-radicals, including straight or branched chain radicals of from 1 to 6 carbon atoms, as illustrated by, but not limited to, methyl, ethyl, propyl, iso-propyl, sec-butyl, amyl, hexyl and the like.

As used herein, the term "substituted phenyl" means a phenyl nucleus ring which bears any number and kind of substituents including loweralkyl, halogen, loweralkoxy, nitro, hydroxy and the like.

The compounds of this invention can generally be prepared as shown in the following scheme wherein R, $X_1$ and $X_2$ are as defined above:

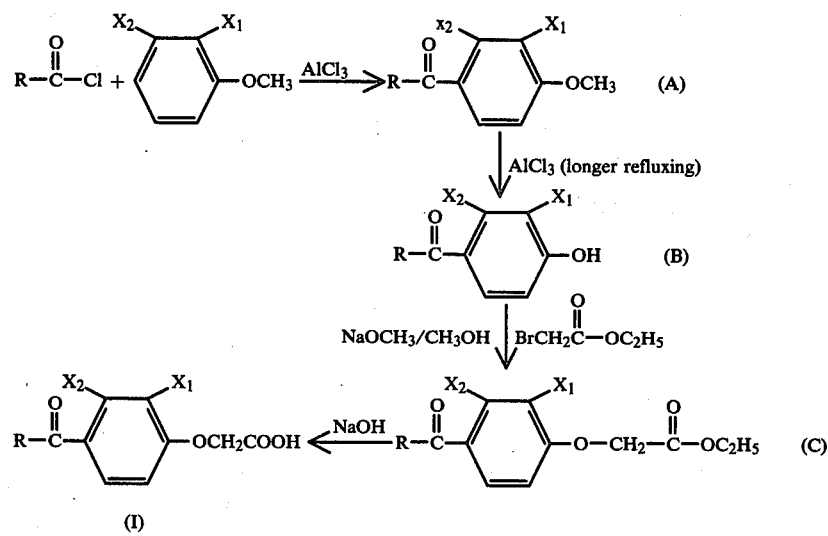

In the above process scheme, the intermediate (A) is prepared by a Friedel-Crafts acylation of the disubstituted anisole by the appropriately substituted acid chloride. The diacyl ketone (A) can be demethylated by any of the usual methods. In the above process, a Lewis acid, aluminum chloride, was used. The anion of the phenol (B) is produced by any base in an appropriate solvent, e.g., $Na_2CO_3$ in acetone or sodium methoxide in methanol, and alkylated by chloroethyl acetate. Hydrolysis of the ester (C) provides the desired acid. It should be understood that even though the route of from (A) to (B) to (C) to the product was used, the route of adding the acid directly to the phenol (D) could have also been used as shown in the following scheme wherein R, $X_1$ and $X_2$ are as defined above:

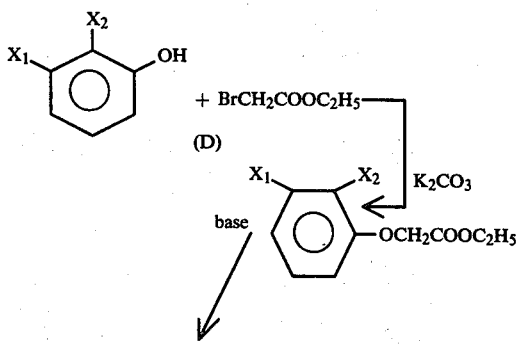

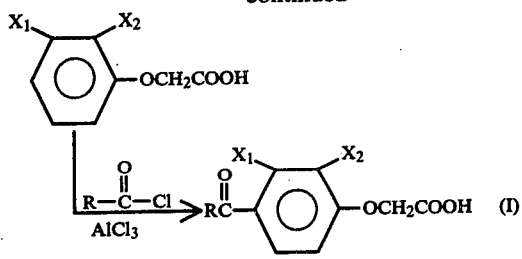

Some of the compounds produced by the general process scheme, illustrated above, which come within the scope of formula (I) are:

4-(4-fluorobenzoyl)-2,3-dichlorophenoxy acetic acid of the formula

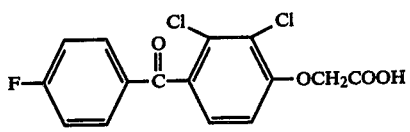

4-(3-chlorobenzoyl)-2,3-dichlorophenoxy acetic acid of the formula

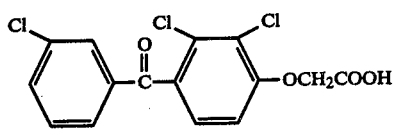

4-(3,4-dichlorobenzoyl)-2,3-dichlorophenoxy acetic acid of the formula

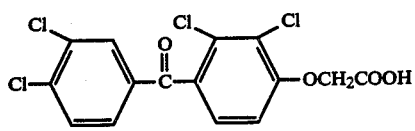

4-(3-methylbenzoyl)-2,3-dichlorophenoxy acetic acid of the formula

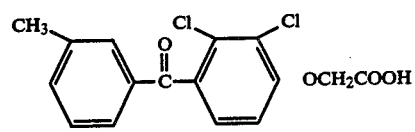

4-(4-methoxybenzoyl)-2,3-dichlorophenoxy acetic acid of the formula

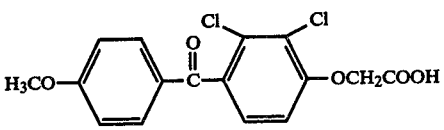

4-(4-hydroxybenzoyl)-2,3-dichlorophenoxy acetic acid of the formula

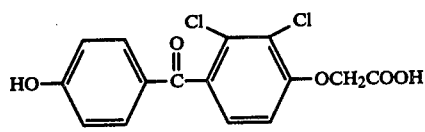

4-(4-nitrobenzoyl)-2,3-dichlorophenoxy acetic acid of the formula

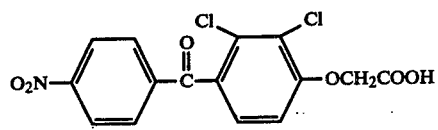

4-(3-fluorobenzoyl)-2,3-dichlorophenoxy acetic acid of the formula

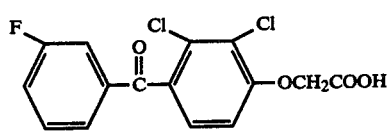

4-(4-chlorobenzoyl)-2,3-dichlorophenoxy acetic acid of the formula

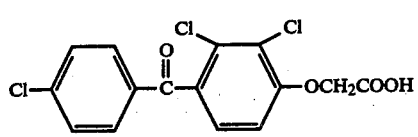

4-(2-fluorobenzoyl)-2,3-dichlorophenoxy acetic acid of the formula

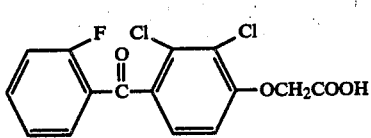

4-(4-methylbenzoyl)-2,3-dichlorophenoxy acetic acid of the formula

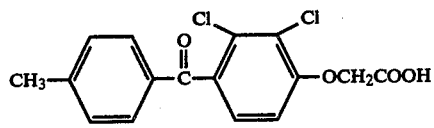

4-(1-naphthoyl)-2,3-dichlorophenoxy acetic acid of the formula

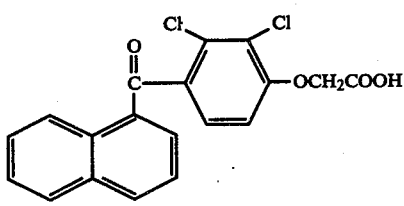

4-(4-fluorobenzoyl)-2,3-dimethyl phenoxy acetic acid sodium salt of the formula

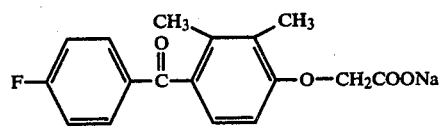

[4-(4-fluorobenzoyl)-1-naphthyloxy]acetic acid of the formula

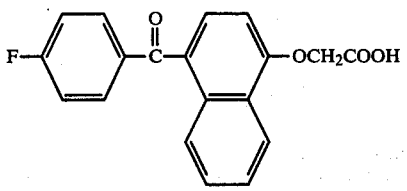

5-[(4-fluorobenzoyl)-2,3-dichlorophenoxymethyl]tetrazole of the formula

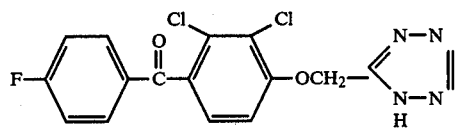

5-[(4-benzoyl)-2,3-dichlorophenoxymethyl]tetrazole of the formula

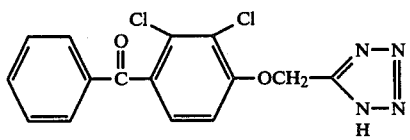

5(4-fluorobenzoyl)-2,3-dimethyl phenoxy methyl tetrazole of the formula

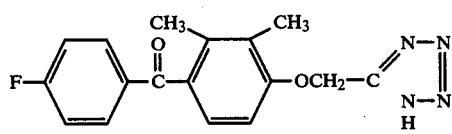

The present compounds have particular activity as uricosuric-diuretic and antihypertensive agents. In contrast to the presently available antihypertensive diuretics, these compounds will produce potential diuretics and antihypertensive effects without the retention of uric acid. In fact, the compounds actually promote the excretion of uric acid which makes them superior to all other available drugs or compounds in this therapeutic category. These drug compounds may be used alone for the treatment of hypertension and edema due to any cause or may be used in conjunction with other diuretics and antihypertensives which have a propensity or activity for the retention of uric acid. The surprising characteristic of the present compounds is that they will reduce the blood pressure as well as increase the excretion of uric acid in warm-blooded animals. The present compound may be administered to warm-blooded animals orally or parenterally. It would be generally administered with a pharmaceutical carrier.

The term "pharmaceutical carrier" for the purpose of the present invention, is intended to refer to any medium that is suitable for the preparation of a dosage unit form and thus includes the tablet medium, pharmaceutically acceptable vehicle or solvent such as is ordinarily used in the preparation of any intravenous or intramuscular solution.

A pharmaceutical composition containing the compound can be administered without danger to warm-blooded animals in parenteral or oral dosage form. For oral administration, amounts of from 0.01 to 200 mg./kg. per day per patient are extremely useful, with the total dose of about 3 grams per day being a suitable range for large animals including humans. The whole dosage range described increases the total uric acid excretion from about 1.5 to about 6.5 in most animals. From these figures it is apparent that the new uricosuric diuretic composition is particularly effective in increasing the excretion of uric acid from most animals.

For all dosage forms, the above illustrated compounds can be placed in capsules, formulated into pills, wafers or tablets in a usable fashion together with a pharmaceutical carrier well known in the art. Tablets may be prepared for immediate release of the active compounds or they may be made enteric, i.e., whereby the active ingredient is released slowly over a period of several hours from within the intestinal tract.

In order to further illustrate the manner in which the above compounds may be prepared and the properties and efficacy of the compounds, reference is made to the following examples, which however, are not meant to limit or restrict the scope of the invention in any respect.

EXAMPLE 1

Preparation of 4(4-Fluorobenzoyl)-2,3-Dichlorophenoxy Acetic Acid

Step (A) 4(4-Fluorobenzoyl)-2,3-dichloroanisole

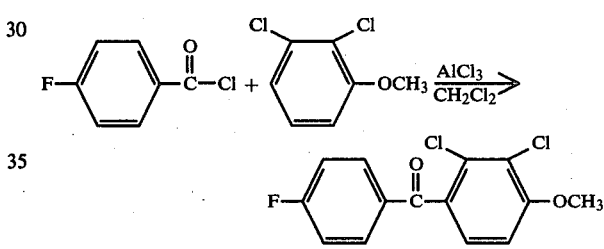

A mixture of 2,3-dichloroanisole (35.4 g.; 0.20 mole), 4-fluorobenzoyl chloride (34.8 g.; 0.22 mole) and methylene chloride (300 ml.) at 5° C. was stirred vigorously and treated with finely powdered aluminum chloride (28.0 g.; 0.21 mole). The reaction mixture was slowly heated and refluxed for two hours. The reaction mixture was cooled to room temperature and decomposed with ice and hydrochloric acid (50 ml.). The aqueous solution was extracted twice with methylene chloride. The combined methylene chloride solution was washed with aqueous sodium bicarbonate solution and finally with water. The organic layer was dried (MgSO₄) and filtered. The solvent was removed in vacuo, and the residue on triturating with pet. ether gave the product 32 g. (50%); m.p. 138°–140°. This product was used for Step B without further purification.

Step (B) 4-(4-Fluorobenzoyl)-2,3-dichlorophenol

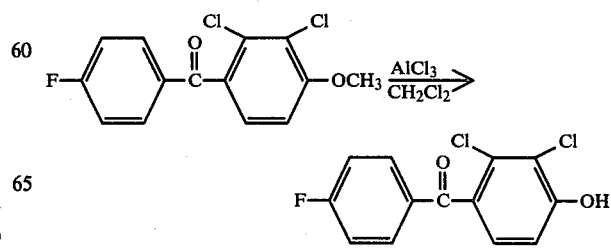

A solution of 23.3 g. (0.078 mole) of 4(4-fluorobenzoyl)-2,3-dichloroanisole in 300 ml. of methylene chloride was treated slowly with 30.5 g. (0.23 mole) of AlCl₃ and the dark mixture thus obtained was refluxed overnight. The reaction mixture was cooled to room temperature and decomposed with ice water. The aqueous phase was extracted with methylene chloride and the combined organic solution was extracted with a cold solution of 10% sodium hydroxide in water. The alkaline solution was acidified with concentrated hydrochloric acid and the resulting precipitate was dissolved in ethylacetate, dried (MgSO₄) and vacuum evaporated. The residue was triturated with pet. ether and the product was collected by filtration and dried to yield 16.0 g. (72%); m.p. 157°–159°. This product was used in Step C without further purification.

Step (C) 4(4-Fluorobenzoyl)-2,3-dichlorophenoxy acetic acid

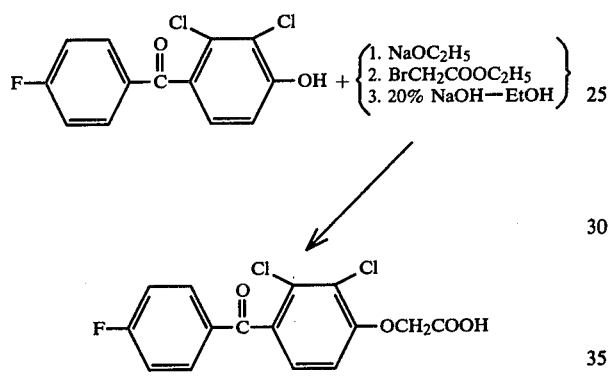

Into a solution of 1.4 g. (0.06 g. atom) of sodium in 200 ml. of absolute alcohol, 16.0 g. (0.056 mole) of 4(4-fluorobenzoyl)-2,3-dichlorophenol was added and the mixture was stirred for thirty minutes at room temperature. The excess of alcohol was vacuum removed and the residue was washed with ether to obtain the sodium salt. The sodium salt of 4(4-fluorobenzoyl)-2,3-dichlorophenol was dissolved in 200 ml. of ethanol and 10.5 g. (0.06 mole) of ethyl bromoacetate was added and the reaction mixture was refluxed for 16 hours, filtered and the solvent was removed in vacuo. The residue was triturated with pet. ether and filtered to obtain a solid product. The product obtained was dissolved in 150 ml. ethanol and 50 ml. of 20% NaOH aqueous solution was added. The reaction mixture was refluxed for ½ hour and the solvent was partially removed in vacuo. The residue was dissolved in hot water and filtered. The hot filtrate was acidified with concentrated hydrochloric acid at 60° C. The resulting precipitate was collected by filtration and washed with water. Recrystallization from dichloroethane afforded 8.0 g. (47%) of the product; m.p. 174°–176°.

Analysis Calcd. for C₁₅H₉Cl₂FO₄: C, 52.48; H, 2.63; Cl, 20.70. Found: C, 52.68; H, 2.63; Cl, 20.78.

EXAMPLE 2

Preparation of 5-[(4-benzoyl)-2,3-dichlorophenoxymethyl]-tetrazole

Step (A) 4-Benzoyl-2,3-dichlorophenol

4-Benzoyl-2,3-dichlorophenol, m.p. 123°–126° was synthesized according to the method of Example 1 (steps A and B), using benzoyl chloride in place of 4-fluorobenzoyl chloride. This product was used for the next step without further purification.

Step (B) 4-Benzoyl-2,3-dichlorophenoxyaceto nitrile

A mixture of 26.70 g. (0.10 mole) of 4-benzoyl-2,3-dichlorophenol, 7.40 g. (0.10 mole) of chloroaceto nitrile, 10.40 g. (0.15 mole) of anhydrous K₂CO₃ and catalytic amount of KI in 200 ml. of acetone was refluxed overnight. The residue was triturated with ether and the product was collected by filtration and dried to yield 22.80 g. (75%); m.p. 110°–112°. This product was used in the next step without further purification.

Step (C) 5[(4-Benzoyl)-2,3-dichlorophenoxymethyl]-tetrazole

A mixture of 30.60 g. (0.1 mole) of 4-benzoyl-2,3-dichlorophenoxyacetonitrile, 7.80 g. (0.12 mole) of NaN₃ and 15.96 g. (0.12 mole) of AlCl₃ in 100 ml. of THF was refluxed for 24 hours. The reaction mixture was cooled and poured in dilute HCl. The solid obtained was filtered and recrystallized from benzene. Yield 26.80 g. (75%); m.p. 184°–186°.

Analysis Calcd. for: C₁₅H₁₀Cl₂N₄O₂: C, 51.58; H, 2.87; N, 16.05. Found: C, 51.44; H, 2.82; N, 16.15.

EXAMPLE 3

4(3-Chlorobenzoyl)-2,3-Dichlorophenoxy Acetic Acid

4(3-Chlorobenzoyl)-2,3-dichlorophenoxy acetic acid, m.p. 155°–156°, was prepared according to the method of Example 1, using 3-chlorobenzoyl chloride in place of 4-fluorobenzoyl chloride.

Analysis Calcd. for $C_{15}H_9Cl_3O_4$: C, 50.08; H, 2.50; Cl, 29.70. Found: C, 49.86; H, 2.46; Cl, 30.53.

EXAMPLE 4

4(3,4-Dichlorobenzoyl)-2,3-Dichlorophenoxy Acetic Acid

4(3,4-Dichlorobenzoyl)-2,3-dichlorophenoxy acetic acid, m.p. 165°–167°, was prepared according to the method of Example 1, using 3,4-dichlorobenzoyl chloride in place of 4-fluorobenzoyl chloride.

Analysis Calcd. for $C_{15}H_8Cl_{11}O_4$: C, 45.70; H, 2.00; Cl, 36.05. Found: C, 45.67; H, 2.19; Cl, 34.06.

EXAMPLE 5

4-(3-Methylbenzoyl)-2,3-Dichlorophenoxy Acetic Acid

4(3-Methylbenzoyl)-2,3-dichlorophenoxy acetic acid, m.p. 173°–175°, was prepared according to the method of Example 1, using 3-methylbenzoyl chloride in place of 4-fluorobenzoyl chloride.

Analysis Calcd. for $C_{16}H_{12}Cl_2O_4$: C, 56.64; H, 3.54; Cl, 20.95. Found: C, 56.58; H, 3.52; Cl, 21.23.

EXAMPLE 6

4-(4-Methoxybenzoyl)-2,3-Dichlorophenoxy Acetic Acid 4-(4-Methoxybenzoyl)-2,3-dichlorophenoxy acetic acid, m.p. 158°–159°, was prepared according to the method of Example 1, using 4-methoxybenozyl chloride in place of 4-fluorobenzoyl chloride.

Analysis Calcd. for $C_{16}H_{12}Cl_2O_5$: C, 54.09; H, 3.38; Cl, 20.00. Found: C, 52.70; H, 2.94; Cl, 20.76.

EXAMPLE 7

Preparation of 4-(4-Hydroxybenzoyl)-2,3-Dichlorophenoxy Acetic Acid

A mixture of 4-(4-methoxybenzoyl)-2,3-dichlorophenoxy acetic acid (3.55 g., 0.01 mole) and hydriodic acid (7.5 ml.) was refluxed at 180°–190° C. for 4 hours. The reaction mixture was concentrated and the solid residue was stirred with water for one hour and filtered. The solid obtained was dissolved in ether and dried ($MgSO_4$). The solvent was removed in vacuo and the residue was recrystallized from ether—pet. ether mixture to give 2 g. (60%) of the product; m.p. 218°–219° C.

Analysis Calcd. for $C_{15}H_{10}Cl_2O_5$: C, 52.78; H, 2.93; O, 23.46. Found: C, 52.61; H, 3.18; O, 23.12.

EXAMPLE 8

4(4-Chlorobenzoyl)-2,3-Dichlorophenoxy Acetic Acid

4(4-Chlorobenzoyl)-2,3-dichlorophenoxy acetic acid, m.p. 196°–198°, was prepared according to the method of Example 1, using 4-chlorobenzoyl chloride in place of 4-fluorobenzoyl chloride.

Analysis Calcd. for $C_{15}H_9Cl_3O_4$: C, 50.08; H, 2.50; O, 17.80. Found: C, 49.86; H, 2.44; O, 16.95.

EXAMPLE 9

4(2-Fluorobenzoyl)-2,3-Dichlorophenoxy Acetic Acid

4(2-Fluorobenzoyl)-2,3-dichlorophenoxy acetic acid, m.p. 161°–162°, was prepared according to the method of Example 1, using 2-fluorobenzoyl chloride in place of 4-fluorobenzoyl chloride.

Analysis Calcd. for $C_{15}H_9FCl_2O_4$: C, 52.48; H, 2.63. Found: C, 52.48; H, 2.60.

EXAMPLE 10

4-(3-Fluorobenzoyl)-2,3-Dichlorophenoxy Acetic Acid 4-(3-Fluorobenzoyl)-2,3-dichlorophenoxy acetic acid, m.p. 166°–168° was prepared according to the method of Example 1, using 3-fluorobenzoyl chloride in place of 4-fluorobenzoyl chloride.

Analysis Calcd. for $C_{15}H_9Cl_2FO_4$: C, 52.48; H, 2.63. Found: C, 52.48; H, 2.60.

EXAMPLE 11

4-(4-Nitrobenzoyl)-2,3-Dichlorophenoxy Acetic Acid

4(4-Nitrobenzoyl)-2,3-dichlorophenoxy acetic acid, m.p. 172°–175°, was prepared according to the method of Example 1, using 4-nitrobenzoyl chloride in place of 4-fluorobenzoyl chloride.

Analysis Calcd. for $C_{15}H_9Cl_2NO_6$: C, 48.60; H, 2.44; N, 3.78. Found: C, 48.33; H, 2.44; N, 3.67.

EXAMPLE 12

4(4-Methylbenzoyl)-2,3-Dichlorophenoxy Acetic Acid

4(4-Methylbenzoyl)-2,3-dichlorophenoxy acetic acid, m.p. 176°–177°, was prepared according to the method of Example 1, using 4-methylbenzoyl chloride in place of 4-fluorobenzoyl chloride.

Analysis Calcd. for $C_{16}H_{12}Cl_2O_4$: C, 56.61; H, 3.54; Cl, 20.94. Found: C, 56.75; H, 3.57; Cl, 20.88.

EXAMPLE 13

4-(1-Naphthoyl)-2,3-Dichlorophenoxy Acetic Acid 4-(1-Naphthoyl)-2,3-dichlorophenoxy acetic acid, m.p. 173°–175°, was prepared according to the method of Example 1, using 1-naphthoyl chloride in place of 4-fluorobenzoyl chloride.

Analysis Calcd. for $C_{19}H_{12}Cl_2O_4$: Cl, 18.93. Found: Cl, 19.00.

EXAMPLE 14

4(4-Fluorobenzoyl)-2,3-dimethylphenoxy acetic acid sodium salt

4(4-Fluorobenzoyl)-2,3-dimethyl phenoxy acetic acid sodium salt, m.p. 203°–205°, was prepared according to the method of Example 1, using 2,3-dimethyl anisole in place of 2,3-dichloro anisole.

EXAMPLE 15

[4-(4-Fluorobenzoyl)-1-naphthyloxy]acetic acid 4-(4-Fluorobenzoyl)-1-naphthyloxy acetic acid, m.p. 105°–108°, was prepared according to the method of Example 1, using 1-methoxynaphthalene in place of 2,3-dichloroanisole.

EXAMPLE 16

Several tests have been made to determine the antihypertensive, diuretic and uricosuric activities of the present alkanonic acid compounds, and to compare such activity with that of known compounds. The tests have been made with the following compounds:

(I) 4-(4-Fluorobenzoyl)-2,3-dichlorophenoxy acetic acid (II) 4-(2-Thienylketo)-2,3-dichlorophenoxy acetic acid

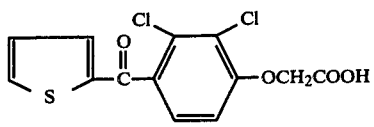

(III) 4(4-Nitrobenzoyl)-2,3-dichlorophenoxy acetic acid (IV) 4-Benzoyl-2,3-dichlorophenoxy acetic acid
(V) 4-(4-Methoxybenzoyl)-2,3-dichlorophenoxy acetic acid
(VI) 4-(4-Chlorobenzoyl)-2,3-dichlorophenoxy acetic acid
(VII) 4-(4-Hydroxybenzoyl)-2,3-dichlorophenoxy acetic acid Compound (II), as described in U.S. Pat. No. 3,758,506, is a known diuretic.

TEST 1

Antihypertensive Activity in Genetically Hypertensive (SH) Rats

In this test, adult male SH rats of the Okamoto strain were trained to be restrained in a wire mesh cylinder for measurement of blood pressure. One half hour prior to blood pressure measurement, the rats were placed in a warm chamber maintained at a constant temperature of 36° C. An occluding cuff, attached to a programmed sphygmomanometer, was placed near the base of the tail of each rat and the pressure in the cuff was increased automatically from 0 to 250 mm Hg at a rate of 10 mm Hg per second. The cuff was then deflated at the same rate. The total time required for each cycle of inflation and deflation of the cuff was 50 seconds and the interval between successive cycles was one minute. A photocell was placed distal to the cuff to sense the arterial pulse wave. As the pressure in the cuff increased, the pulse wave completely disappeared when the cuff pressure just exceeded the systolic arterial blood pressure. During deflation, the pulse wave reappeared at approximately the same pressure. Five interferencefree signals obtained during deflation were recorded for each rat. Only those rats with a systolic blood pressure of 180 mm Hg or more during the control period were used in this study. A model 7 Grass polygraph was used to record the cuff pressure and the arterial pulse wave. The heart rate of the rat was computed from the record of the arterial pulse wave.

The compounds tested were administered orally to the rats, repeatedly for four consecutive days as recorded below in Table I.

TABLE I

Antihypertensive Effect of Diuretic Compounds By Repeated Oral Administration In Spontaneously Hypertensive Rats

| Day | Hour | | Compound (I) N = 8 | | Compound (I) N = 7 | | Compound (II) N = 4 | |
|---|---|---|---|---|---|---|---|---|
| | | | Mean | S.E.M. | Mean | S.E.M. | Mean | S.E.M. |
| 1 | −1 | Control Blood Pressure (mm Hg) | 226.4$^a$ | ± 3.2 | 226.9 | ± 3.7 | 215.3 | ± 5.0 |
| | | Control Heart Rate (beats/min) | 367.5 | ± 18.9 | 374.3 | ± 20.3 | 380.0 | ± 33.7 |
| | | | PERCENT CHANGE | | | | | |
| | 0 | FIRST DOES: | 30 MPK | | 100 MPK | | 100 MPK | |
| | 3 | Blood Pressure | −4.6 | ± 0.9 | −13.0* | ± 1.1 | −5.8 | ± 3.4 |
| | | Heart Rate | −6.3 | ± 3.6 | −21.1 | ± 4.8 | −4.5 | ± 6.6 |
| 2 | 24 | Blood Pressure | −0.1 | ± 2.0 | −13.3* | ± 1.5 | −5.0 | ± 3.1 |
| | | Heart Rate | 7.5 | ± 4.9 | −10.1 | ± 7.7 | −1.8 | ± 10.9 |
| | 25 | SECOND DOSE: | 30 MPK | | 100 MPK | | 100 MPK | |
| 3 | 48 | Blood Pressure | −5.8 | ± 1.2 | −15.9* | ± 2.1 | −12.5 | ± 6.4 |
| | | Heart Rate | 3.8 | ± 7.8 | −10.7 | ± 7.4 | −5.5 | ± 7.8 |
| | 49 | THIRD DOSE: | 30 MPK | | 100 MPK | | 100 MPK | |
| 4 | 72 | Blood Pressure | −12.1* | ± 2.2 | −16.1* | ± 2.2 | −8.3 | ± 3.8 |
| | | Heart Rate | −8.0 | ± 3.6 | −24.4 | ± 6.5 | 2.5 | ± 6.0 |
| | 73 | FOURTH DOSE: | 30 MPK | | 100 MPK | | 100 MPK | |
| 5 | 96 | Blood Pressure | −11.8* | ± 2.2 | −19.4* | ± 3.0 | −9.5 | ± 2.6 |
| | | Heart Rate | −11.0 | ± 5.7 | −22.1 | ± 4.6 | −3.0 | ± 11.8 |

$^a$Mean ± S.E.M.
*Statistically significant at $P \leq 0.05$ by analysis of variance.

As shown in Table I, compound (I) exhibited a statistically significant antihypertensive activity at both tested doses of 30 and 100 mg./kg. With the dose of 30 mg./kg. of Compound (I), the blood pressure of the hypertensive rats fell significantly at the third day of administration. No statistically significant antihypertensive effect was observed in rats receiving this dosage of compound (II).

With the dose of 100 mg./kg., the effect of compound (I) on the blood pressure was apparent already at the interval of three hours after the first administration. No statistically significant antihypertensive effect was observed in rats given the same dosage of Compound (II).

In view of the results shown in Table I, Compound (I) clearly exhibited antihypertensive effects in SH rats at doses where compound (II) was inactive.

TEST 2

Diuretic and Saluretic Activity in Genetically Hypertensive (SH) Rats

In this test, male genetically hypertensive (SH) rats, weighing 250–350 grams, were used. The rats were loaded with 0.9% sodium chloride solution, the volume of the load being five percent of their body weight. At the same time, the rats were dosed with the drugs to be tested and placed individually in stainless steel metabolism cages. No food or water was given to the animals during the test. Urine was collected at hourly intervals during the first eight hours and at the 24-hour interval following drug administration. The volume of excreted urine was accurately measured at each time interval.

Pooled urine samples at time intervals of 2, 8 and 24 hours were analyzed for sodium, potassium, and chloride ions and for uric acid. Sodium and potassium were estimated using a Digital Readout Flame Photometer (Instrumentation Labs.). Chloride was estimated by the method of Shales and Shales (J. Biol. Chem., 140:879, 1941). Uric acid was determined by a colorimetric-uricase method adapted according to an American Monitor Corporation procedure using Beckman's DSA-560 colorimeter.

Compounds (I) and (II) were orally administered in various comparable doses. Each dose was tested in at least eight rats. Controls received vehicle (0.5% methylcellulose), orally administered in the same volume of 2 ml./kg. Statistical analysis of the data was done by student's t-test.

The results of the tests are recorded below in Tables 2 and 3.

TABLE 2

Diuretic and Saluretic Effects of Compound (I) In Saline-Loaded Spontaneously Hypertensive Rats

| TIME INTERVAL (hours) | URINARY MEASUREMENTS | CONTROL+ | Compound (I) (mg/kg) 30 | CONTROL | Compound (I) (mg/kg) 300 |
|---|---|---|---|---|---|
| 0-2 | VOLUME (ml) | 4.6 ± 0.6 | 7.9 ± 0.7* | 5.2 0.6 | 12.2 ± |
|  | URIC |  |  |  |  |
|  | SODIUM (μEq) | 525.9 ± 59.9 | 885.2 ± 95.3* | 666.76 ± 121.2 | 1390.1 ± 87.1* |
|  | POTASSIUM (μEq) | 380.2 ± 56.5 | 460.5 ± 38.5 | 306.7 ± 42.1 | 536.0 ± 35.1* |
|  | CHLORIDE (μEq) | 709.9 ± 94.6 | 1129.6 ± 86.6* | 689.2 ± 135.4 | 1646.5 ± 95.3* |
|  | Na/K RATIO | 1.5 ± 0.2 | 1.9 ± 0.1* | 2.1 ± 0.3 | 2.7 ± 0.2 |
|  | URIC ACID (μg) | 282.0 ± 26.5 | 387.3 ± 70.9 | 173.5 ± 14.3 | 271.4 ± 16.2* |
| 2-8 | VOLUME (ml) | 8.7 ± 1.1 | 7.8 ± 0.9 | 8.4 ± 0.9 | 18.4 ± 1.5* |
|  | SODIUM (μEq) | 1256.7 ± 113.3 | 1210.4 ± 151.8 | 1128.6 ± 128.3 | 2516.3 ± 164.5* |
|  | POTASSIUM (μEq) | 520.0 ± 44.6 | 592.4 ± 116.0 | 523.0 ± 34.1 | 769.6 ± 125.8 |
|  | CHLORIDE (μEq) | 1383.2 ± 132.0 | 1388.8 ± 165.6 | 1194.2 ± 118.2 | 2624.0 ± 213.4* |
|  | Na/K RATIO | 2.5 ± 0.2 | 2.3 ± 0.3 | 2.1 ± 0.2 | 3.7 ± 0.5* |
| URIC ACID (μg) | 668.0 ± 48.5 | 507.4 ± 58.7*d | 502.7 ± 44.0 | 854.9 ± 68.4* |  |
| 8-24 | VOLUME (ml) | 6.1 ± 0.7 | 5.3 ± 0.7 | 10.3 ± 1.1 | 8.1 ± 1.2 |
|  | SODIUM (μEq) | 940.7 ± 92.2 | 772.8 ± 83.8 | 1256.8 ± 188.0 | 871.5 ± 84.4 |
|  | POTASSIUM (μEq) | 616.6 ± 54.2 | 725.4 ± 113.6 | 849.7 ± 45.3 | 946.2 ± 88.4 |
|  | CHLORIDE (μEq) | 701.7 ± 73.9 | 481.6 ± 83.9 | 1150.6 ± 167.2 | 597.8 ± 87.2*d |
|  | Na/K RATIO | 1.5 ± 0.1 | 1.2 ± 0.2 | 1.4 ± 0.2 | 1.0 ± 0.1*d |
|  | URIC ACID (μg) | 1988.9 ± 136.0 | 1859.1 ± 194.0 | 1489.9 ± 89.0 | 2431.4 ± 163.0* |

+ Mean, S.E.M.; N = 8
*p ≤ 0.05 using Student's t-test
d Decrease

TABLE 3

Diuretic and Saluretic Effects Of Compound (II) In Saline-Loaded Spontaneously Hypertensive Rats

| TIME INTERVAL (hours) | URINARY MEASUREMENTS | CONTROL++ | Compound (II) (mg/kg) 3+ | 10+ |
|---|---|---|---|---|
| 0-2 | VOLUME (ml) | 4.98 ± 0.63 | 4.41 ± 0.70 | 4.45 ± 0.76 |
|  | SODIUM (μEq) | 572.1 ± 88.8 | 555.1 ± 94.3 | 577.9 ± 115.0 |
|  | POTASSIUM (μEq) | 216.9 ± 28.8 | 200.4 ± 29.5 | 262.4 ± 39.6 |
|  | CHLORIDE (μEq) | 597.6 ± 89.9 | 552.1 ± 107.4 | 651.7 ± 127.6 |
|  | Na/K RATIO | 2.66 ± 0.24 | 2.66 ± 0.26 | 2.12 ± 0.14 |
|  | URIC ACID (μg) | 254.7 ± 22.0 | 298.5 ± 21.7 | 310.8 ± 33.7 |
| 2-8 | VOLUME (ml) | 8.69 ± 0.90 | 7.84 ± 1.02*d | 9.84 ± 1.25 |
|  | SODIUM (μEq) | 1169.6 ± 125.6 | 926.1 ± 152.9*d | 1224.8 ± 152.9 |
|  | POTASSIUM (μEq) | 486.6 ± 51.8 | 482.6 ± 36.3*d | 535.2 ± 28.6 |
|  | CHLORIDE (μEq) | 1200.5 ± 137.4 | 903.4 ± 135.5*d | 1288.0 ± 121.4 |
|  | Na/K RATO | 2.54 ± 0.17 | 1.95 ± 0.33 | 2.31 ± 0.27 |
|  | URIC ACID (μg) | 608.7 ± 52.0 | 588.6 ± 49.9*d | 703.9 ± 44.0 |
| 8-24 | VOLUME (ml) | 7.66 ± 0.61 | 8.43 ± 1.04 | 7.56 ± 0.87 |
|  | SODIUM (μEq) | 1078.6 ± 87.2 | 1043.2 ± 179.1 | 1022.3 ± 127.5 |
|  | POTASSIUM (μEq) | 719.4 ± 54.4 | 820.6 ± 86.1 | 737.2 ± 91.8 |
|  | CHLORIDE (μEq) | 803.1 ± 74.5 | 748.0 ± 149.7 | 778.5 ± 131.9 |
|  | Na/K RATIO | 1.73 ± 0.24 | 1.35 ± 0.22 | 1.53 ± 0.24 |
|  | URIC ACID (μg) | 1759.2 ± 107.2 | 1661.5 ± 98.2*9 | 1823.4 ± 84.7 |
|  |  |  | 30+ | 100+ |
| 0-2 | VOLUME (ml) | 4.98 ± 0.63 | 4.84 ± 0.83 | 7.70 ± 1.16 |
|  | SODIUM (μEq) | 572.1 ± 88.8 | 634.7 ± 103.9 | 1047.6 ± 114.5 |
|  | POTASSIUM (μEq) | 216.9 ± 28.8 | 194.4 ± 28.0 | 362.1 ± 42.0 |
|  | CHLORIDE (μEq) | 597.6 ± 89.9 | 595.4 ± 106.4 | 1157.4 ± 126.8* |
|  | Na/K RATIO | 2.66 ± 0.24 | 3.40 ± 0.42 | 3.15 ± 0.60 |
|  | URIC ACID (μg) | 254.7 ± 22.0 | 252.1 ± 28.0 | 402.6 ± 30.6* |
| 2-8 | VOLUME (ml) | 8.69 ± 0.90 | 6.86 ± 0.79 | 10.71 ± 0.78 |
|  | SODIUM (μEq) | 1169.6 ± 125.6 | 932.4 ± 75.6 | 1412.9 ± 117.4 |
| POTASSIUM (μEq) |  | 486.6 ± 51.8 | 375.5 ± 40.3 | 693.4 ± 46.3 |
|  | CHLORIDE (μEq) | 1200.5 ± 137.4 | 908.0 ± 72.9 | 1474.6 ± 112.2 |
|  | Na/K RATO | 2.54 ± 0.17 | 2.59 ± 0.17 | 2.09 ± 0.21 |

TABLE 3-continued

Diuretic and Saluretic Effects Of Compound (II) In Saline-Loaded Spontaneously Hypertensive Rats

| TIME INTERVAL (hours) | URINARY MEASUREMENTS | CONTROL++ | Compound (II) (mg/kg) | |
|---|---|---|---|---|
| | URIC ACID (μg) | 608.7 ± 52.0 | 565.3 ± 43.8 | 925.6 ± 64.6* |
| 8–24 | VOLUME (ml) | 7.66 ± 0.61 | 7.86 ± 1.07 | 7.08 ± 1.00 |
| | SODIUM (μEq) | 1078.6 ± 87.2 | 963.7 ± 112.6 | 871.0 ± 114.1 |
| | POTASSIUM (μEq) | 719.4 ± 54.4 | 834.5 ± 93.8 | 660.1 ± 106.2 |
| | CHLORIDE (μEq) | 803.1 ± 74.5 | 835.4 ± 104.2 | 678.4 ± 151.0 |
| | Na/K RATIO | 1.73 ± 0.24 | 1.18 ± 0.11 | 2.00 ± 0.88 |
| | URIC ACID (μg) | 1759.2 ± 107.2 | 1536.9 ± 104.6 | 1968.8 ± 89.2 |
| | | | 300+ | |
| 0–2 | VOLUME (ml) | 4.98 ± 0.63 | 9.01 ± 0.85* | |
| | SODIUM (μEq) | 572.1 ± 88.8 | 1238.5 ± 125.3* | |
| | POTASSIUM (μEq) | 216.9 ± 28.8 | 292.1 ± 34.5 | |
| | CHLORIDE (μEq) | 597.6 ± 89.9 | 1287.2 ± 126.6* | |
| | Na/K RATIO | 2.66 ± 0.24 | 4.41 ± 0.46* | |
| | URIC ACID (μg) | 254.7 ± 22.0 | 403.7 ± 47.9* | |
| 2–8 | VOLUME (ml) | 8.69 ± 0.90 | 11.58 ± 0.98 | |
| | SODIUM (μEq) | 1169.6 ± 125.6 | 1516.8 ± 105.6 | |
| | POTASSIUM (μEq) | 486.6 ± 51.8 | 668.4 ± 41.9 | |
| | CHLORIDE (μEq) | 1200.5 ± 137.4 | 1597.8 ± 123.7 | |
| | Na/K RATIO | 2.54 ± 0.17 | 2.28 ± 0.12 | |
| | URIC ACID (μg) | 608.7 ± 52.0 | 921.1 ± 66.0* | |
| 8–24 | VOLUME (ml) | 7.66 ± 0.61 | 7.18 ± 0.70 | |
| | SODIUM (μEq) | 1078.6 ± 87.2 | 680.7 ± 51.7*d | |
| | POTASSIUM (μEq) | 719.4 ± 54.4 | 772.0 ± 120.8 | |
| | CHLORIDE (μEq) | 803.1 ± 74.5 | 538.0 ± 69.4*d | |
| | Na/K RATIO | 1.73 ± 0.24 | 1.54 ± 0.75 | |
| | URIC ACID (μg) | 1759.2 ± 107.2 | 2321.2 ± 171.4 | |

+Mean, S.E.M.; N = 8
++Mean, S.E.M.; N = 20 (a pool of two control groups).
*P ≤ 0.05 using Student's t-test (calculated from control group of the day).
dDecrease As shown above in Tables 2 and 3, Compound (I) exhibited a significant diuretic, natriuretic, and chloruretic activity in spontaneously hypertensive rats at oral dose as low as 30 mg./kg. At the higher dose of 300 mg./kg., these effects were further increased. Compound (I) also caused a significant excretion of uric acid. Compound (II) was much less potent diuretic and saluretic agent in this animals model, even though its profile was similar to that of Compound (I).

As indicated in the results recorded in Tables 2 and 3, Compound I is a potent diuretic, saluretic and uricosuric agent in spontaneously hypertensive rats, and is a much more potent agent than Compound (II).

TEST 3

Diuretic And Saluretic Activity In Spontaneously Hypertensive Rats

This test was performed by a method similar to that of Test 2, above. In this test, Compounds (I), (III), (IV), (V), (VI) and (VII) were administered with a saline load (5% of body weight) to the rats. The results of the test (i.e., excretion of urine, Na, K, Cl and Uric Acid measured over a period of two hours) are provided below in Table 4.

TABLE 4

Diuretic and Saluretic Activity in SH Rats

| COMPOUND | ORAL DOSE (mg/kg) | URINE OUTPUT (ml) | SODIUM EXCRETION (mEq) | POTASSIUM EXCRETION (mEq) | CHLORIDE EXCRETION (mEq) | URIC ACID EXCRETION (mg) | Na/K RATIO |
|---|---|---|---|---|---|---|---|
| (III) | C+ | 6.8 | 0.78 | 0.36 | 0.96 | 0.24 | 2.36 |
| | 300 | 11.0* | 1.41* | 0.45 | 1.77* | 0.22 | 3.14 |
| (IV) | C | 4.6 | 0.60 | 0.21 | 0.64 | 0.21 | 3.02 |
| | 300 | 8.7* | 1.10* | 0.28 | 1.26* | 0.31 | 4.16* |
| (V) | C | 7.0 | 0.69 | 0.40 | 0.78 | 0.23 | 1.66 |
| | 300 | 11.9* | 1.32* | 0.54 | 1.75* | 0.39* | 2.51* |
| (VI) | C | 6.1 | 0.68 | 0.32 | 0.77 | 0.27 | 2.25 |
| | 30 | 8.2 | 0.97* | 0.48* | 1.20* | 0.27 | 2.08 |
| (VII) | C | 5.5 | 0.50 | 0.35 | 0.54 | 0.22 | 1.45 |
| | 30 | 10.4* | 1.21* | 0.40 | 1.35* | 0.21 | 2.96* |
| (I) | C | 4.6 | 0.53 | 0.38 | 0.71 | 0.28 | 1.47 |
| | 30 | 7.9* | 0.88* | 0.46 | 1.13* | 0.39 | 1.92* |

+C group of eight control rats of the same body weight tested together with rats dosed with particular compound.
*Statistical significance: p ≤ 0.05 using student's t-test

TEST 4

Uricosuric And Diuretic Activity In Anesthetized Cebus Monkeys (*Cebus Capucinus*)

In this test, female Cebus monkeys weighing 1.3–1.8 kg. were immobilized with phenylcyclidine hydrochloride, 1 mg./kg. intramuscularly, and anesthetized with sodium pentobarbital, 15 mg./kg. intravenously. The trachea was incised just caudal to the larynx and was cannulated. One femoral artery was cannulated to record arterial blood pressure and the other to collect blood samples. One femoral vein was cannulated for infusion of solutions and the other was used for drug administration. The urinary bladder was catheterized through the urethral opening for collection of urine samples. Lead II electrocardiogram was recorded to monitor the heart rate.

On completion of surgical preparation of the monkey, a priming dose of inulin, 50 mg./kg. (20 mg./ml. solution) was administered intravenously. It was followed by an infusion of inulin in a concentration suitable to deliver 4 mg./min. The infusion rate was adjusted to deliver 0.38 ml./min. The infusion solution also included, in addition to inulin, uric acid in a concentration suitable to deliver 0.6 mg./kg./min., 0.15% lithium carbonate and 5% mannitol. The test drug was dissolved or suspended in the same solution that contained the priming dose of inulin (that is, a single dose of the given drug was injected at the beginning of the experiment).

The bladder was emptied and the urine was discarded at the time of priming with inulin. Urine samples were collected every 30 minutes thereafter. The last sample was collected at 270 minutes. The volume of each urine sample was measured and recorded. Two ml. blood samples were collected at the midpoint of the interval between collection of two urine samples and the blood samples were centrifuged to obtain plasma. Analysis of the plasma and urine was done to determine osmolality and the concentration of sodium, potassium, chloride, inulin and uric acid.

Compounds (I) and (II) were administered intravenously in comparable doses, whereas Compound (III), (IV), (V), (VI) and (VII) were administered in a dose of 50 mg./kg.

The results of the test are provided below in Tables 5 and 6.

TABLE 5

Uricosuric and Diuretic Effects of Compounds (I) and (II) In Anesthetized Cebus Monkeys

| | I.V. DOSE (mg/kg) | N | URIC ACID EXCRETION (mg/kg/120 min) | URINE FLOW (ml/kg) 30 min | URINE FLOW (ml/kg) 120 min |
|---|---|---|---|---|---|
| CONTROL (Placebo) | — | 4 | 5.05* ± 0.54 | 12.1 ± 2.4 | 33.9 ± 5.0 |
| COMPOUND (I) | 6.25 | 4 | 13.60 ± 1.78 | 12.4 ± 2.7 | 41.4 ± 3.8 |
| | 12.50 | 2 | 20.23 ± 0.21 | 12.1 ± 5.8 | 40.9 ± 18.4 |
| | 25.00 | 4 | 19.50 ± 2.27 | 20.3 ± 2.0 | 53.2 ± 2.0 |
| | 50.00 | 1 | 27.45 | 18.7 | 42.1 |
| COMPOUND (II) | 10.00 | 2 | 12.69 ± 4.35 | 11.8 ± 5.3 | 36.8 |
| | 30.00 | 2 | 16.79 ± 2.52 | 11.3 ± 1.6 | 32.8 ± 0.1 |
| | 100.00 | 2 | 16.20 ± 0.63 | 15.8 ± 2.2 | 32.4 ± 3.9 |

*Mean ± S.E.M.

As shown in Table 5, Compound (I) exhibited significant uricosuric and diuretic effects, when given intravenously to the anesthetized Cebus monkey. In both activities, i.e., uricosuric and diuretic, Compound (I) is clearly more potent than Compound (II).

TABLE 6

Uricosuric And Diuretic Activity In Anesthetized Cebus Monkeys

| COMPOUND | I.V. DOSE (mg/kg) | N | URIC ACID EXCRETION (mg/kg/120 min) | URINE FLOW (ml/kg) 30 min | URINE FLOW (ml/kg) 120 min |
|---|---|---|---|---|---|
| CONTROL (Placebo) | — | 4 | 5.05* ± 0.54 | 12.1 ± 2.4 | 33.9 ± 5.0 |
| (III) | 50 | 2 | 20.33 ± 0.23 | 21.61 ± 1.39 | 60.90 ± 3.23 |
| (IV) | 50 | 2 | 19.40 ± 1.27 | 25.57 ± 2.47 | 43.30 ± 3.26 |
| (V) | 50 | 2 | 19.61 ± 0.69 | 29.98 ± 4.52 | 68.42 ± 2.08 |
| (VI) | 50 | 2 | 19.35 ± 0.58 | 12.05 ± 2.74 | 39.37 ± 3.03 |
| (VII) | 50 | 2 | 19.55 ± 0.42 | 18.00 ± 2.08 | 41.40 ± 4.52 |

*Mean ± S.E.M.

Compounds (III), (IV), (V), (VI) and (VII), as shown in Table 6, all have substantial uricosuric and diuretic activity, when given intravenously to the anesthetized Cebus monkeys.

EXAMPLE 17

Antidiuretic and Antidipsogenic Effect Of 4-(4-Fluorobenzoyl)-2,3-Dichlorophenoxy Acetic Acid In Rats With Hereditary Hypothalamic Diabetes Insipidus In this experiment, the antidiuretic and antidipsogenic effect of Compound (I) of Example 16, 4-(4-fluorobenzoyl)-2,3-dichlorophenoxy acetic acid, in rats with diabetes insipidus was determined.

Eleven rats were used in this experiment, including males and females suffering from hereditary hypothalamic diabetes insipidus (Brattleborro Strain) with the average body weight of the rats being 242±16 grams. The rats were placed individually in metal metabolic cages and their water intake and urine output were measured daily. The effect of 4-(4-fluorobenzoyl)-2,3-dichlorophenoxy acetic acid (Compound I) on the fluid turnover in these animals was tested according to the following experimental schedule:

Day:
1—control period
2—control period
3—Compound (I), 30 mg./kg.
4—Compound (I), 100 mg./kg.

5—Compound (I), 300 mg./kg.
8—control period
9—control period

The values of the fluid turnover, measured on two consecutive days before and after the testing of Compound (I) were averaged. Compound (I) was administered orally, suspended in 0.5% methylcellulose in a total volume less than 1 cc.

The results of the experiment are summarized below, in Table 7. The results indicate that Compound (I) exhibited a significant, dose-dependent antidiuretic effect in rats with hereditary hypothalamic diabetes insipidus. The drug dependent decrease of the excessive urine output is accompanied by a corresponding dose-dependent decrease in the spontaneous drinking in these animals.

TABLE 7

Effect of 4-(4-Fluorobenzoyl)-2,3-Dichlorophenoxy Acetic Acid (Compound I) On The Fluid Turnover In Rats With Hereditary Hypothalamic Diabetes Insipidus

|  | CONTROL* before testing | COMPOUND I (mg/kg) | | | CONTROL* after testing |
| --- | --- | --- | --- | --- | --- |
|  |  | 30 | 100 | 300 |  |
| URINE OUTPUT (ml/100 g B.W./24 hrs.) | 71.9+ ± 6.9 | 52.9 ± 6.2 | 31.9 ± 4.0 | 22.3 ± 2.7 | 65.3 ± 7.1 |
| WATER INTAKE (ml/100 g B.W./24 hrs.) | 84.0 ± 8.0 | 62.0 ± 7.0 | 37.0 ± 4.0 | 24.0 ± 3.0 | 72.0 ± 9.0 |

*Average of two consecutive daily values
+Mean ± S.E.M.

As shown by the results in Table 7, above, the compound 4-(4-fluorobenzoyl)-2,3-dichlorophenoxy acetic acid demonstrated good efficacy in the treatment of the diabetes insipidus in rats. From the results it can therefore be expected to be effective in the treatment of diabetes insipidus in man.

We claim:

1. A compound of the formula

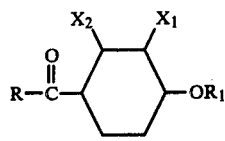

wherein R is a phenyl ring, a phenyl ring substituted with a substituent selected from the group consisting of loweralkyl of from 1 to 6 carbon atoms, halogen, loweralkoxy of from 1–6 carbon atoms, nitro and hydroxy, or naphthyl; $R_1$ is methylene-5-tetrazole; and $X_1$ and $X_2$ are each the same halogen or a loweralkyl of 1–6 carbon atoms, or when taken together form with the two attached carbons a phenyl ring.

2. A compound according to claim 1, wherein R is 3-chlorophenyl, and $X_1$ and $X_2$ are each chlorine.

3. A compound according to claim 1, wherein R is 4-fluorophenyl, and $X_1$ and $X_2$ are each chlorine.